(12) United States Patent
Voelz

(10) Patent No.: US 6,200,585 B1
(45) Date of Patent: Mar. 13, 2001

(54) ANIMAL EYE PROTECTOR

(76) Inventor: Michael H. Voelz, 3076 W. 850 North, Delphi, IN (US) 46923

(*) Notice: Subject to any disclaimer, the term of this patent is extended or adjusted under 35 U.S.C. 154(b) by 0 days.

(21) Appl. No.: 09/177,352

(22) Filed: Oct. 23, 1998

(51) Int. Cl.[7] .................................................. A01N 25/08
(52) U.S. Cl. ............................ 424/411; 424/400; 424/401; 424/409; 424/443; 424/447; D29/109; D29/102; D29/106; 128/97.1; 128/857; 128/858; 119/712; 119/715; 119/729
(58) Field of Search ............................ 119/715, 814, 119/836, 853, 855, 729; 424/402, 403, 410, 411, 427, 443, 445, 447, 448; D29/108, 102, 106; D30/151; 128/97.1, 857, 858

(56) References Cited

U.S. PATENT DOCUMENTS

| D. 158,020 | * | 4/1950 | Spier | D29/108 |
| 468,238 | * | 2/1892 | Cather | 119/836 |
| 2,616,081 | * | 11/1952 | Weaver et al. | D29/108 |
| 2,882,858 | * | 4/1959 | Dlugi | 119/853 |
| 3,302,646 | * | 2/1967 | Behney | 128/260 |
| 4,317,239 | * | 3/1982 | Bryska | 2/411 |
| 4,549,539 | | 10/1985 | Donaldson | 128/132 |
| 4,787,372 | * | 11/1988 | Ramseyer | 128/94 R |
| 5,127,423 | | 7/1992 | Draeger | 128/849 |
| 5,540,189 | * | 7/1996 | Masson | 119/814 |
| 5,597,559 | | 1/1997 | Olejnik et al. | 424/78.04 |
| 5,778,826 | * | 7/1998 | Dillon et al. | 119/717 |

* cited by examiner

Primary Examiner—Neil S. Levy
(74) Attorney, Agent, or Firm—Andrus, Sceales, Starke & Sawall, LLP

(57) ABSTRACT

An apparatus for maintaining the eyes of an animal, such as a dog or cat, closed during surgery to keep the surface of the eyes moist. The apparatus includes a collar, a head pad connected to the collar and positioned between an animals ears on its forehead, and a pair of straps also connected to the collar positioned to extend from beneath the animal's chin over the animal's eyes and to be fastened to the head pad. The head pad and straps cooperate to pinch or force together loose skin above and below the eyes to close the eyelids and prevent drying out thereof. A lead line extending from the collar attaches to a non-movable structure so that when the animal awakens, the movement of the animal pulls the collar loose from around the neck.

8 Claims, 2 Drawing Sheets

ANIMAL EYE PROTECTOR

BACKGROUND OF THE INVENTION

This invention relates in general to animal husbandry. More specifically, the present invention relates to a device for holding the eyes of an animal closed when anesthesia is administered during surgery, or any time it is desired to hold one or both eyes of an animal closed.

When a veterinarian performs surgery on an animal, the animal is usually anesthetized with an agent that causes its eyes to remain open. The anesthesia thus prevents the normal blinking mechanism from keeping the surface of the eye moist. Exposure of a non-blinking eye to air causes it to quickly dry out. When the cornea of the eye dries, it may cause corneal ulcers, a painful eye condition which must be medically treated to prevent infection and pain for the animal.

Currently, the standard practice in animal surgery is to rub a thick ophthalmic ointment, such as that disclosed in U.S. Pat. No. 5,597,559, into the eye in an attempt to maintain the eye's moisture when the eye is continuously open. However, even with ointment in the animal's eye, the corneal surface still dries out and corneal ulcers can result.

In human surgery, when a patient's eyes stay open from anesthesia, numerous devices are available to prevent the patient's eyes from drying out and causing corneal ulcers. The most common of these is a piece of medical adhesive tape attached at one end directly to the eyelid of the patient and at its other end to the cheek below the eye which keeps the eyelid shut and prevents drying of the cornea. In animals with fur-covered skin, however, tape will not stick to the fur and, therefore, cannot be used to hold the eyelid closed.

U.S. Pat. No. 4,549,539 describes a surgical device for protecting an eye that uses two adhesive strips interconnected by a releasable stud-and-tab fastener, one strip placed on the upper eyelid of a person and the other on the cheek below the eye to keep the eyelid closed. This device also requires direct adhesion of the strips to the skin, which, as noted above, is not practical for a fur covered animal.

U.S. Pat. No. 5,127,423 discloses a surgical eye cover for protecting human eyes during ophthalmic surgery. The cover comprises a first plastic film applied securely to the patient's face over the eyes, the first film having a window cut into it to permit access to the patient's eye, and a pair of overlapping cover flaps forming a second plastic film that covers the open window of the first film. However, this device requires adhesion to the skin to function, and is, as the previous devices are, not practical for use on fur-covered animals.

SUMMARY OF THE INVENTION

It is an object of the present invention to provide a device for holding the eyes of an animal closed during surgery, during an examination, or at any other time requiring one or both eyes to be held closed. The present invention prevents the eye surface from drying out, and thus minimizes or completely eliminates corneal surface damage to the eye, by using the natural moisturizing system of the eye.

It is another object of the present invention to provide a device for holding an animal's eyes closed that can be used with fur-covered animals.

It is yet another object of the present invention to provide a device that is simple and inexpensive in construction and, therefore, disposable after use to prevent the spread of disease or infection from one animal to another.

A further object of the invention is to provide a device which is lightweight, can be easily applied to the animal and can be easily removed without injuring the animal.

A still further object of the invention is to provide an eye closing device that self-releases when the animal awakens from anesthesia.

In accordance with the present invention, there is provided an eye closing arrangement which engages skin adjacent to at least one eye of an animal to cause this skin to push the eyelid to cover the animal's eye, and a harness for releasably securing the eye closing arrangement in place on the animal. Preferably, the harness comprises a collar attachable around an animal's neck which is releasably securing around the animal's neck in any conventional manner. For example, hook and loop fasteners, adhesive or a buckle and catch may be used to fasten the two loose ends of the collar together. However, although a collar is preferred, any type of mechanism for securing the eye closing arrangement in place on the animal may be employed.

The eye closing arrangement includes a first member which engages skin above the animal's eye and a second member which engages skin below the animal's eye, and fastening means for releasably fastening the first and second members together so that these members cooperate to substantially pinch or force the skin above and below the eye together to close the eyelid. Preferably, the first member comprises a head pad connected to the collar and positioned so that when the collar is around the animal's neck, the head pad extends between the animal's ears on the animal's forehead to a point just above the animal's eyes. The second member preferably comprises a chin strap also connected to the collar and positioned so that when the collar is around an animal's neck, the chin strap extends from beneath the animal's chin over one eye of the animal and toward the animal's forehead. Fastening means is use to releasably fasten the chin strap to the head pad and thereby pinch or force the skin above and below the animal's eye together to close the eyelid. Preferably, the fastening means is an adhesive located on the end of the chin strap, but as noted above, could also be hook and loop fasteners, or any other conventional fastening mechanism, if desired, depending upon the particular animal being treated.

In order to maintain the other eye of the animal closed, the apparatus further includes a second chin strap connected to the collar and positioned so that when the collar is around the animal's neck, the second chin strap extends from beneath the animal's chin over the other eye of the animal toward the animal's forehead. This second chin strap also includes fastening means for releasably fastening it to the head pad so that in use, the chin strap and head pad cooperate to pinch or force the skin above and below the animal's second eye together to close the second eyelid in the same manner as for the first eye. Depending upon the animal being treated, the chin straps may extend in a criss-cross relation from the collar. This enables better positioning of the straps to bear against the appropriate skin area to ensure complete closing of the animal's eyes.

DETAILED DESCRIPTION OF THE PREFERRED EMBODIMENT

Figure 1:
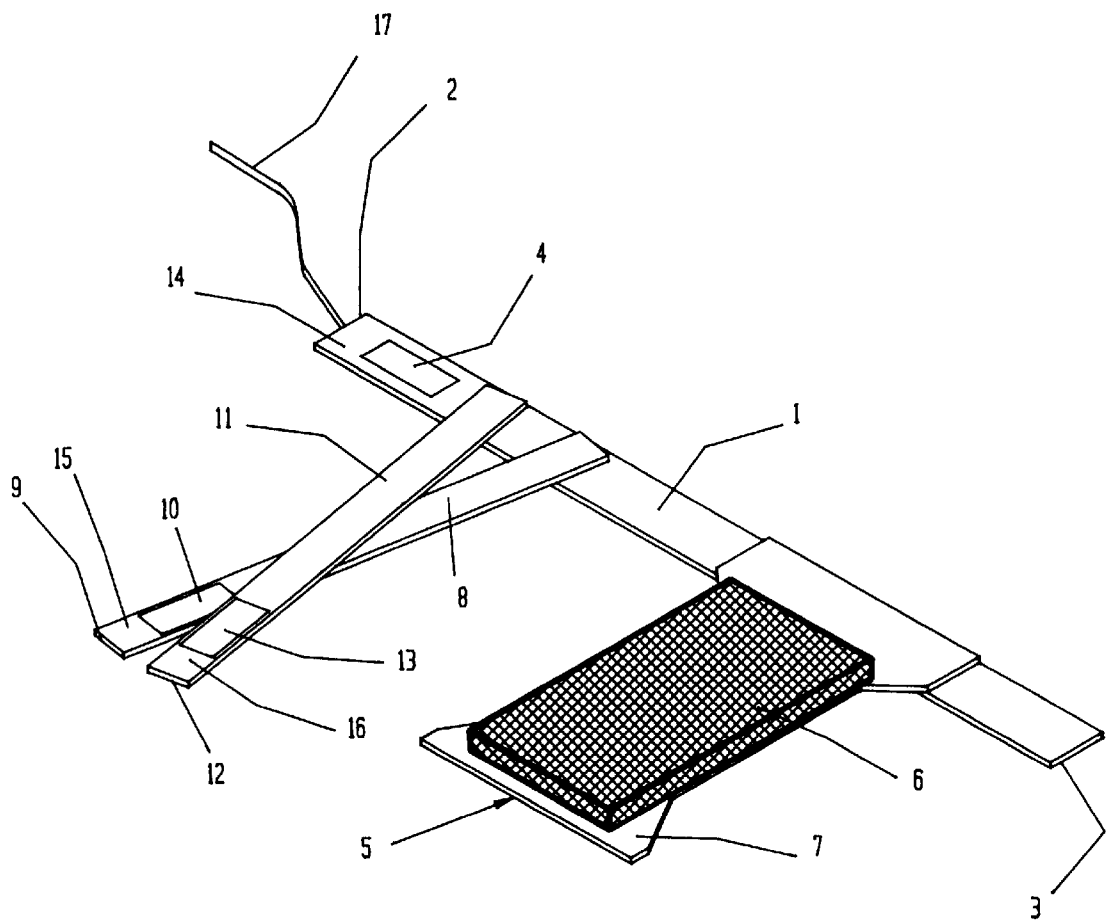
FIG. 1 is a perspective view of an animal eye protector constructed according to the present invention.
Figure 2:
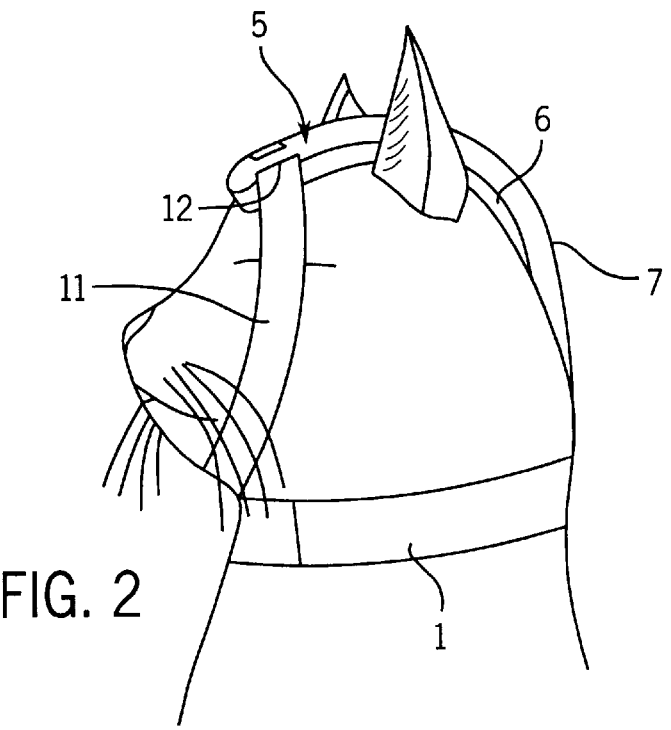
FIG. 2 is a side elevational view of the animal eye protector illustrated in use on a cat.
Figure 3:
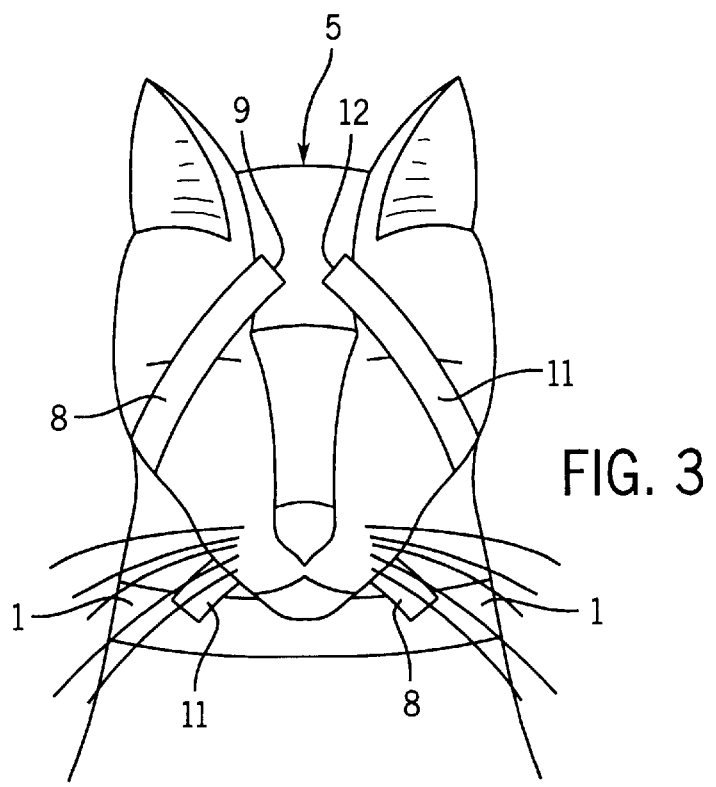
FIG. 3 is a front elevational view of the animal eye protector.

Referring now to the drawings, FIGS. 1–3 illustrate an animal eye protector that maintains an animal's eye closed constructed in accordance with the present invention. The eye closing arrangement may be composed of any suitable material such that it may be used once and disposed of thus preventing potential spread of disease or parasites between animals. However, depending upon the materials of construction, the eye closing arrangement could also be sanitized and reused if desired.

Referring now to FIG. 1, there is illustrated a preferred embodiment of the eye closing arrangement. As illustrated, the eye closing arrangement includes a harness in the form of a collar 1 of sufficient length to wrap around an animal's neck. Such a harness enables the eye closing arrangement to be secured in place without requiring attachment to the animal's fur. As shown, collar 1 comprises a narrow, relatively thin band having opposite free ends 2 and 3 that overlap one another when placed around the animal's neck. Adhesive 4 on end 2 is used to secure the collar in place about the animal's neck. End 2 extends beyond adhesive 4 to allow a finger tab 14 to be present for grasping when applying and removing the collar 1. The length of collar 1 may be varied depending upon the particular animal being treated. Thus, for example, collar 1 would be relatively long if utilized with a large dog such as a Great Dane as compared to an eye closing arrangement which might be used with a house cat. Adhesive 4 may be any suitable type of adhesive, but preferably may be double sided adhesive tape such as 3M brand PN021200-13266 or a hook and loop attachment mechanism such as that available under the trade name Velcro.

The eye closing arrangement of the present invention functions by engaging loose skin adjacent to at least one eye of the animal to cause the skin to push the eyelids closed to cover the eye. This is accomplished by utilizing a first member that engages and moves skin above the eye downward toward the eye. Alternately, a second member may be used that engages skin below the eye and moves it upwardly toward the eye thereby effectively closing the eye. These members can be utilized either alone or in combination to accomplish the desired result of utilizing the loose skin adjacent the eye to push the eyelid closed and keep the eye moist. When used in combination, the two members cooperate to substantially pinch the skin above and below the eye together to close the eyelids.

In order to accomplish this, a head pad 5 is connected to collar 1 adjacent end 3 and extends substantially perpendicularly therefrom. Although illustrated as being rectangular in shape, head pad 5 may be formed in any shape depending upon the particular animal being treated and the configuration of that animal's head, ears, forehead, etc. As illustrated, however, head pad 5 is comprised of a foam panel 6 glued to a sheet 7. Preferably, sheet 7 is formed of the same material as collar 1 and may be sewn thereto, adhesively bonded thereto, or integrally formed with collar 1. The head pad 5 is dimensioned to have a width substantially equivalent to the width between the animal's ears, and during use extends over the animal's forehead to just above each eye of the animal. The foam panel 6 is pliable and flexible which thus allows it to conform to the shape of the animal's head. The foam panel 6 serves to push and hold in place the loose skin located above the animal's eye downwardly toward the eye during application of the eye closing arrangement. As seen best in FIG. 2, foam panel 6 extends to a point just adjacent or above the animal's eye but does not touch the animal's eye. By varying the shape of foam panel 6, the eye closing arrangement of the present invention can be modified to fit various animal species and sizes. Also, by varying the stiffness, size and shape of foam panel 6, the pressure on the skin above the animal's eye can be adjusted. In a preferred embodiment, sheet 7 and foam panel 6 will typically initially be oversized to allow one size to fit most animals. The oversized head pad 5 may then be conformed to the animal being treated by cutting sheet 7 and foam panel 6 to the proper length and shape before applying the eye closing arrangement to the animal's head. Foam panel 6 may be made of any conventional material, but is preferably made of resilient polyurethane or natural or synthetic rubber.

As noted above, the eye closing arrangement also includes a second member engaging skin below the eye which cooperates with a first member such as head pad 5 to substantially pinch or force together the skin above and below the animal's eye to close the eye. This second member comprises a chin strap 8 connected to collar 1 adjacent end 2 thereof. As shown in FIG. 1, chin strap 8 extends at an acute angle from collar 1 and includes a free end 9 having adhesive 10 thereon. Free end 9 extends beyond adhesive 10 to provide a finger tab 15 for grasping strap 8 during application and removal. Adhesive 10 functions to secure strap 8 to sheet 7 when the eye closing arrangement is in use, as will hereinafter be described.

Likewise, a second chin strap 11 extends from collar 1 at an opposite complementary acute angle so that straps 8 and 11 extend in criss-cross relation from collar 1. Chin strap 11 also includes a free end 12 having adhesive 13 thereon. Free end 12 extends beyond adhesive 13 to provide a finger tab 16 for grasping strap 11 during application and removal. Adhesive 13 also functions to fasten chin strap 11 to the exterior surface of sheet 7, as will hereinafter be described. Although illustrated in a criss-cross relation, chin straps 8 and 11 need not necessarily cross one another depending upon a particular animal being treated. However, as illustrated in FIGS. 2 and 3, the eye closing arrangement of the present invention is shown in use with a domestic cat. Thus, the criss-cross relation of straps 8 and 11 provide the proper orientation for forcing loose skin below the cat's eye upwardly to close the eye. As illustrated, straps 8 and 11 have a length sufficient to extend from beneath the animal's chin over one eye of the animal and overlap pad 5 so that adhesive 10 and 13, respectively, may effectively fasten straps 8 and 11 to head pad 5 thereby closing both eyes. The width of straps 8 and 11 may also vary depending upon the animal being treated, but are preferably approximately the same width of the animal's eye. This insures loose skin is displaced during application to shift the skin toward the eye, pushing the eyelids closed to cover the eye. As with head pad 5, straps 8 and 11 may be attached to collar 1 in any conventional manner as, for example, sewn thereto, integrally formed therewith, or adhesively bonded thereto. In addition, straps 8 and 11 could be riveted to collar 1 which would enable straps 8 and 11 to be pivotably attached to collar 1. Such pivotal attachment would provide additional flexibility for properly positioning straps 8 and 11 with respect to the animal's eyes. Also, by varying the position, straps 8 and 11 are attached to collar 1, the eye closing arrangement may be adapted for small versus large animals. Smaller animals would require that straps 8 and 11 be positioned closer to head pad 5 whereas larger animals would result in straps 8 and 11 being connected to collar 1 at a location closer to free end 2.

Referring now to FIGS. 2 and 3, the eye closing arrangement is illustrated as being in use on a domestic cat. In order to apply the eye closing arrangement, a user would merely secure collar 1 around the cat's neck with head pad 5 positioned to extend between the animal's ears on the animal's forehead. The skin on top of the animal's head would be shifted toward the animal's eyes with one hand while pad 5 is held in place with the other hand. Pad 5 is then held down with one hand to maintain the loose skin shifted toward the eyes. Strap 8 or 11 would then be extended from beneath the animal's chin, over one eye of the animal and fastened to sheet 7 of head pad 5. The other chin strap would likewise be extended to cover the other eye of the animal and be fastened to head pad 5. During this process, the outer edge of foam panel 6 engages the loose skin above the animal's eye to displace it downwardly while strap 8 or 11 engages the loose skin beneath the animal's eye to displace it upwardly to thereby pinch or force the skin together to close the animal's eyelids. The amount of pressure keeping the eye closed may be adjusted by varying the location strap 8 or 11 is fastened to head pad 5. The further upwardly strap 8 or 11 is attached to head pad 5, the more pressure there is on the skin above and below the animal's eye and correspondingly more pressure pinching the skin together to close the eyelids.

To remove the device, one simply pulls on free ends 9 and 12 of straps 8 and 11 respectively to displace them from head pad 5. Thereafter, end 2 is pulled from end 3 to release collar 1. As noted, the device may then be thrown away, or sanitized and reused if desired.

In addition, end 2 may have an additional lead line or member 17 extending from collar 1 and attached at end 2 which allows end 2 to be anchored to a cage wall or floor of an animal's quarters. Thus, when the animal begins to awaken from anesthesia, the animal's movements will put tension on end 2 via member 12 and pull end 2 of the collar loose from around the neck of the animal and effectively remove collar 1 from the animal as it awakens (FIG. 1).

There has been illustrated and described an eye closing arrangement or device which fulfills all the objects and advantages sought therefore. The arrangement or device utilizes a harness which does not require attachment to the eyes or to the animal's fur, and can be utilized with numerous animal species.

I claim:

1. An apparatus for maintaining an animal's eye closed, comprising:

a collar for an animal having skin covered with fur or feathers and having an eye with an eyelid moveable to a closed position over said eye;

securing means for releasably securing said collar around an animal's neck;

a head pad connected to said collar and positioned so that when said collar is around an animal's neck the head pad extends between an animal's ears on an animal's forehead to a location closely adjacent to and above an animal's eye;

a chin strap connected to said collar and positioned so that when said collar is around an animal's neck the chin strap extends from beneath an animal's chin over one eye of said animal; and fastening means for releasably fastening said chin strap to said head pad whereby said chin strap and head pad cooperate to cause said head pad to move downwardly toward said eye thereby moving the eyelid to said closed position to cover said eye.

2. The apparatus of claim 1 wherein said collar comprises a thin, narrow band having opposite free ends that overlap one another when placed around an animal's neck.

3. The apparatus of claim 2 wherein said securing means comprises adhesive located at one of said free ends of said collar.

4. The apparatus of claim 1 further including a second chin strap connected to said collar positioned so that when said collar is around the animal's neck the second chin strap extends from beneath the animal's chin over a second eye of said animal, and second fastening means for releasably fastening said second chin strap to said head pad whereby said second chin strap and head pad cooperate to cause said head pad to move downwardly toward said second eye thereby moving the eyelid to said closed position to cover said second eye.

5. The apparatus of claim 4 wherein said chin straps extend in criss-cross relation from said collar.

6. The apparatus of claim 4 wherein the fastening means for said chin strap and the second fastening means for said second chin strap each comprises adhesive.

7. The apparatus of claim 4 where each chin strap extends beyond the adhesive to provide finger grasping tabs.

8. The apparatus of claim 4 further including a lead line for attaching the collar to a non-moveable structure relative to the animal so that when the animal moves, the collar around the animal's neck is pulled loose, allowing the collar to fall off.

* * * * *